(12) United States Patent
Selvam et al.

(10) Patent No.: US 8,715,770 B2
(45) Date of Patent: May 6, 2014

(54) APPARATUSES AND METHODS FOR MICROPARTICLE DRY COATING OF SURFACES

(75) Inventors: Parthiban Selvam, Lawrence, KS (US); Hugh D. C. Smyth, West Lake Hill, TX (US); Martin Donovan, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 13/582,883

(22) PCT Filed: Mar. 9, 2011

(86) PCT No.: PCT/US2011/027797
§ 371 (c)(1), (2), (4) Date: Sep. 14, 2012

(87) PCT Pub. No.: WO2011/112756
PCT Pub. Date: Sep. 15, 2011

(65) Prior Publication Data
US 2012/0328768 A1 Dec. 27, 2012

Related U.S. Application Data

(60) Provisional application No. 61/312,139, filed on Mar. 9, 2010.

(51) Int. Cl.
*B05D 1/12* (2006.01)
*B05C 5/02* (2006.01)

(52) U.S. Cl.
USPC ............ 427/2.1; 427/2.31; 427/180; 118/300

(58) Field of Classification Search
USPC ............................ 427/2.1, 2.31, 180; 118/300
See application file for complete search history.

(56) References Cited

U.S. PATENT DOCUMENTS

| | | | | |
|---|---|---|---|---|
| 4,325,988 | A | * | 4/1982 | Wagner .......................... 427/160 |
| 5,494,520 | A | * | 2/1996 | Lamendola et al. .......... 118/608 |
| 5,655,523 | A | | 8/1997 | Hodson et al. |
| 2004/0037785 | A1 | * | 2/2004 | Staniforth et al. .............. 424/46 |

FOREIGN PATENT DOCUMENTS

| WO | 2008-051433 A2 | 5/2008 |
|---|---|---|
| WO | 2010-014827 A2 | 2/2010 |

OTHER PUBLICATIONS

International Search Report and Written Opinion of PCT/US2011/027797 mailed on Nov. 29, 2011, 10 pages.

* cited by examiner

*Primary Examiner* — Frederick Parker
(74) *Attorney, Agent, or Firm* — Kilpatrick Townsend & Stockton LLP

(57) ABSTRACT

A device for coating dry powder microparticles onto a surface may include a jet mill configured to mill dry powder particles into microparticles having a desired aerodynamic diameter and to deaggregate the microparticles, a feed hopper structured and arranged to feed dry powder particles to the jet mill, a surface configured to receive dry powder microparticles and an exit nozzle associated with the jet mill. The exit nozzle may be arranged to direct deaggregated micronized dry powder particles from the jet mill to the surface to be coated. The device may further include a holder structured and arranged to hold an item, wherein the item includes the surface. In some aspects of the device, the item may be a film.

7 Claims, 2 Drawing Sheets

APPARATUSES AND METHODS FOR MICROPARTICLE DRY COATING OF SURFACES

CROSS-REFERENCE TO RELATED APPLICATIONS

This application claims the benefit of priority of U.S. provisional application No. 61/312,139, entitled "Apparatuses and Methods for Microparticle Dry Coating of Surfaces," filed on Mar. 9, 2010, which is incorporated herein by reference.

TECHNICAL FIELD

The present disclosure relates to systems and methods of microparticle dry coating of surfaces and, more particularly, systems and methods of microparticle dry coating of surfaces using a jet mill, wherein the coated surfaces are for use in a dry powder inhaler platform.

BACKGROUND

The delivery of therapeutics to the lung for the local treatment of pulmonary disorders (asthma, chronic obstructive pulmonary disease (COPD), cystic fibrosis) has long been utilized, and inhalation therapy for the treatment of systemic diseases (e.g. diabetes) has been the focus of increasing academic and industry research within the past decade. Given its extremely large surface area, mild environment, and ease of administration, in contrast to oral and intravenous routes of drug delivery, the lung presents an especially attractive avenue of therapeutic delivery.

However, pulmonary drug delivery is not without its obstacles. For drug particles to deposit in the deep lung, where they exert their therapeutic action, they must possess certain physical properties. Specifically, the drug particles must have an aerodynamic diameter below 5 microns, where the aerodynamic diameter encompasses both the density and geometric diameter of the drug particle. Accordingly, aerosolized drug particles must be less than 5 microns in aerodynamic diameter when they exit an inhaler to deposit in the deep lung.

While both liquid (metered dose inhalers, nebulizers) and solid (dry powder inhalers) dosage forms are used for inhalation therapy, dry powder drug formulations are garnering an increasing share of the market due to their dose flexibility and excellent drug stability. While dry powder formulations offer many advantages over liquid formulations, their performance is plagued by low drug delivery (generally below 30% of the total dose is delivered to the deep lung) and high throat and upper airway deposition. This is evidence that the majority of the drug particles exiting the inhaler are not in the primary particle size (<5 microns), but rather in agglomerates or still attached to carrier particles, which due to their large aerodynamic diameter deposit in the throat and upper airways.

However, due to the micron dimensions of the drug particles, the cohesive forces that exist between them, due primarily to Van der Waals and electrostatic forces, are quite strong and prevent drug particles from being readily deaggregated as they exit the inhaler. Even while the primary particle size (i.e., the size of a single particle of the drug powder) may be below 5 microns in diameter, a large fraction of the dose may comprise agglomerated drug particles many times the size of the primary particles, leading to drug deposition in the mouth, throat, or upper airways (possibly producing toxic side effects) and/or drug deposition in the inhaler (reducing efficiency of the dose).

Drug particle agglomeration may occur before and/or during a coating process. Regardless, one potential problem with dry coating of surfaces (e.g., a film, carrier particle surfaces, or other substrates used in dry powder inhalers) with microparticles of a drug is that drug-drug cohesive interactions are not effectively eliminated. Another possible problem is that press-on forces between the drug microparticles and the surface can be large enough to prevent the detachment of the drug particles from the surface during inhalation.

Thus, the dry coating of surfaces with microparticles is a crucial step in developing an effective dry powder drug delivery platform, as well as in a number of different applications. Research has shown that there is an optimum range for press-on forces during coating; strong enough to adhere the drug to the film surface, yet sufficiently weak so that the drug is readily dispersed during aerosolization. To this end, it may be desirable to provide apparatuses for coating and coating methods capable of modulating the press-on forces between drug and surface during coating.

It may be desirable to provide apparatuses and methods for dosing and coating inhalation powders onto surfaces that deaggregate drug powder into particles of primary size and reduce the presence and subsequent dispersion of drug agglomerates that could undesirably deposit in the mouth and upper airways. It may also be desirable to provide apparatuses and methods for coating surfaces with drug microparticles sized to be deposited in the deep lung, thereby improving the efficacy of current dry powder inhalers.

SUMMARY OF INVENTION

According to various aspects of the disclosure, a device for coating dry powder microparticles onto a surface may include a jet mill configured to mill dry powder particles into microparticles having a desired aerodynamic diameter and to deaggregate the microparticles, a feed hopper structured and arranged to feed dry powder particles to the jet mill, a surface configured to receive dry powder microparticles and an exit nozzle associated with the jet mill. The exit nozzle may be arranged to direct deaggregated micronized dry powder particles from the jet mill to the surface to be coated. The device may further include a holder structured and arranged to hold an item, wherein the item includes the surface. In some aspects of the device, the item may be a film.

In some aspects of the disclosure, a method of coating dry powder microparticles onto a surface may include feeding dry powder particles into a jet mill, milling said dry powder particles into microparticles having a desired aerodynamic diameter, deaggregating the microparticles in the jet mill, and directing said deaggreagated microparticles from the jet mill through a nozzle toward a surface to be coated.

According to various aspects, a method of coating dry powder microparticles onto a surface may include feeding dry powder microparticles into a mixing device, deaggregating the microparticles in the mixing device, and directing said deaggreagated microparticles from the mixing device through a nozzle toward a surface to be coated.

Some further advantages and embodiments may become evident from the attached drawings.

DETAILED DESCRIPTION

Figure 1:
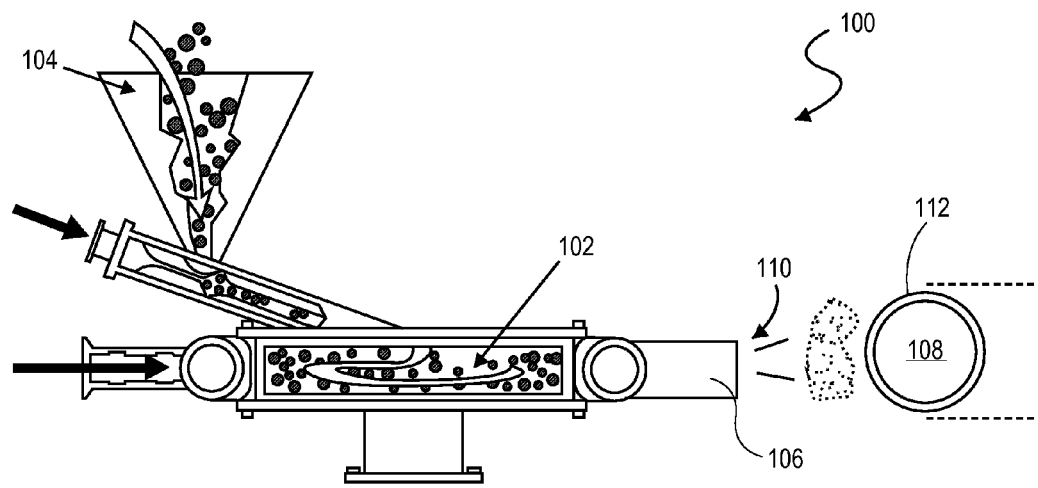
FIG. 1 is a perspective view of an exemplary jet mill coating apparatus in accordance with various aspects of the disclosure.

FIG. 1 illustrates a perspective view of an exemplary apparatus according to the disclosure. Namely, FIG. 1 shows an exemplary coating apparatus 100 for microparticle dry coating of surfaces such as, for example, a film intended for use in a dry powder inhaler. According to various aspects, the coating apparatus 100 may include a jet mill 102, a feeding device 104, an exit nozzle 106, and a holder 108 structured and arranged to hold a surface item to be coated, such as, for example, a film. According to various aspects, the jet mill 102 may be a continuous jet mill or a pulsed jet mill. The jet mill 102 may be a customized jet mill or conventional jet mill selected so as to deaggregate dry powder and reduce particle size to a desired aerodynamic diameter and further modified as discussed below. For example, in some aspects, it may be desirable that the dry particles exit the jet mill 102 with a particle size of less than 5 microns. Thus, if the dry powder supplied to the jet mill contains particles exceeding 5 microns in aerodynamic diameter, the milling process may include grinding and/or otherwise breaking up of the crystalline structure of the dry powder to attain a particle size of less than 5 microns. In currently marketed devices and systems, only 15-30% of the drug loaded in dry powder inhalers is sufficiently deaggregated and dispersed to become respirable. It may be desirable to provide a device that deaggregates a greater percentage of the dry powder to eventually be loaded in the inhaler. When the particle size of the dry powder being supplied is less than 5 microns, the milling process may include a deaggregation step.

Referring to FIG. 1, the feeding device 104 comprises a manual feed hopper configured and arranged to supply dry powder to the jet mill 102. It should also be appreciated that an automated feeder can be employed rather than a manual feeder. For example, the feeder may comprise a vibration feeder, a screw feeder, or the like, all of which would be understood by persons skilled in the art. In any event, the rate of feeding may depend on the type and/or nature of dry powder being fed and the type and/or nature of surface that is being coated.

Conventional jet mills typically include a mechanism for collecting the milled particles such as, for example, a cyclone jar of the like. After the milled particles are collected, the particles are typically processed before being coated onto a carrier member for use in an inhalation device. For example, the milled particles may be mixed with other excipients, blended with substrates, etc. To the contrary, in exemplary devices consistent with the present disclosure, the milled micronized particles are directed from the jet mill 102 through the exit nozzle 106 toward a holder 108 for a surface item to be coated.

The milled particles exit the jet mill 102 via the nozzle 106. The size and shape of the nozzle 106 may play an important role on the film coating. In some aspects, the nozzle 106 may include a coaxial sheath configured to prevent particles from missing the target film, which may be associated with the holder 108. The device may have an adjustable nozzle pressure $P_N$ for moving particles out of the jet mill via the nozzle. The magnitude of the press-on forces of the milled particles onto the film depends on the velocity of the milled particles at the nozzle exit 110. This velocity is a strong function of the size and shape of the nozzle, as would be understood by persons skilled in the art. The higher the velocity, the higher the press-on forces that result. For good aerosol redispersion of particles upon inhalation, lower press-on forces are preferred. Accordingly, the size and shape of the nozzle can be customized based on the desired press-on forces.

According to various aspects, where film surfaces are to be coated, the film holder 108 may be stationary, rotatable, and/or translatable relative to the exit nozzle 106 of the jet mill 102. A film 112 can be held by the holder 108 using well known methods such as the use of rollers and drums and similar equipment. The surface substrate may include any dry powder carrier member, whether a film, powder, granular bed, lactose particle, bead, or other substrate to be used in a dry powder inhaler may also be treated for adhesion prior to coating with drug particles. Such treatments are used to enhance the coating control and uniformity. Treatments include roughening the surface to provide optimal contact area for the adherence of drug particles. In some aspects, corona treatment may be employed to enhance the adhesion and coating of the film using electrostatic attraction and repulsion of drug particles.

Referring again to FIG. 1, the holder 108 holding a target film is placed at a requisite distance from the nozzle 106. The distance between the film 112 and nozzle exit 110 may play an important role on the press-on forces of micronized particles relate to the film. The distance between the film 112 and the nozzle exit 110 is directly proportional to the press-on force. Accordingly, the distance between the film and the nozzle can be selected based on the desired press-on forces.

The film 112 may be either placed stationary or mounted on a movable film holder, for example, a circulating drum, whose axle of rotation is substantially perpendicular to the exit nozzle, as illustrated in the exemplary device of FIG. 1. In the single piece film embodiment of FIG. 1, the film may be wrapped around the surface of the cylindrical holder, as would be understood by persons skilled in the art. However, it should be appreciated that the target film may take the form of a continuous sheet fed via any conventional mechanism to and from a roller or other holder proximal the exit nozzle of the jet mill, as shown in dashed lines in FIG. 1. For example, the film sheet may wrap about a portion of the holder in a manner such that the deaggregated microparticles are directed to the film as it curves with the surface of the roller. In some aspects, a continuous sheet of target film may extend in a substantially linear manner perpendicular to the direction that the microparticles exit the nozzle 106, as shown in the exemplary embodiment of FIG. 5, and the film can be moved linearly in that perpendicular direction.

Figure 2:
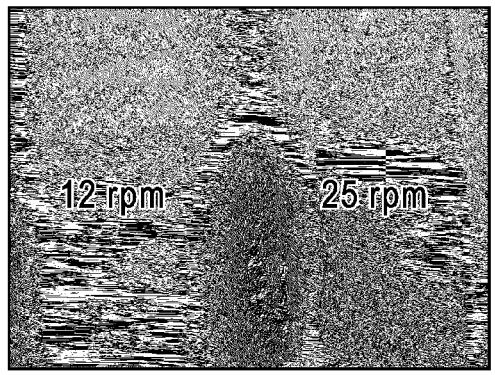
FIG. 2 is an illustration of films coated in accordance with exemplary apparatus and methods of the disclosure.

One possible advantage of a rotating film is that a regular uniform coating may be ensured and agglomeration of particles may be prevented. The rotational speed of the films is an important variable in the film coating. Faster rotational speeds may not produce good coating results as seen in FIG. 2. Accordingly, the rotational speed of the film holder can be selected based on the desired press-on forces.

Example

According to one exemplary embodiment, the drug particle was fed into the jet mill using a hand held hopper at a flow rate of 300 mg/sec. The flow rate of 300 mg/sec was predetermined as it provided a desirable milled particle size. According to some aspects, high flow rates may produce inefficient milling and high polydispersity. The drug was milled at a constant nozzle pressure ($P_N$) and grinding pressures ($P_1$ & $P_2$). The milled particle size depends on these pressures. Table 1 below shows the size of the milled ciprofloxacin particles as a function of these pressures. Based on the results from Table 1, the following pressures, $P_N$=90 psi and $P_1$=$P_2$=100 psi, were selected for this study. In this study, a regular rectangular tube having a 1.5 cm exit diameter was selected as the nozzle to ensure desired press-on forces as well as uniform particle coating. In this study, the film was placed at a distance of 2 cm from the nozzle exit to ensure desired press-on forces, and the film was rotated at 12 rpm.

TABLE 1

| Grinding Pressure ($P_1$ - psi) | Grinding Pressure ($P_2$ - psi) | Nozzle Pressure ($P_N$ - psi) | $d_{50}$ (µm) |
|---|---|---|---|
| 0 | 0 | 0 | 5.74 |
| 100 | 100 | 90 | 2.51 |
| 100 | 100 | 45 | 3.2 |
| 100 | 100 | 10 | 3.53 |
| 50 | 50 | 90 | 3.01 |
| 50 | 50 | 45 | 3.49 |
| 50 | 50 | 10 | 3.72 |

Referring to Table 1, $d_{50}$ refers to the median diameter of particles as determined by laser diffraction and based on the volume of the particles.

Figure 3:
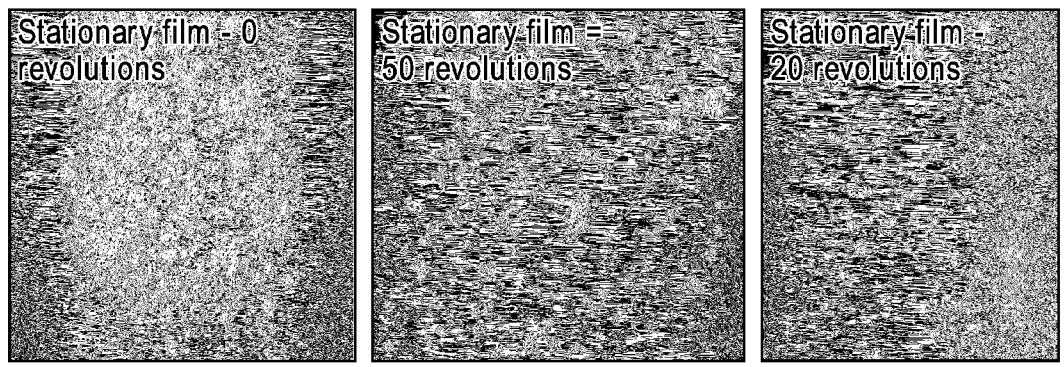
FIG. 3 is an illustration of films coated in accordance with exemplary apparatus and methods of the disclosure.

The drug coating uniformity and concentration on the target film can also be modified by the number of rotations. FIG. 3 shows the differences on the film coating based on the number of rotations. As shown, stationary films may be preferred for higher concentration of particle coating. Table 2 below shows the concentration of drug loading as a function of revolutions.

TABLE 2

| Number of revolutions | Concentration (µg/cm$^2$) |
|---|---|
| 0 | 1123.56 ± 52.34 |
| 20 | 145.67 ± 21.23 |
| 50 | 330.34 ± 45.72 |

Figure 4:
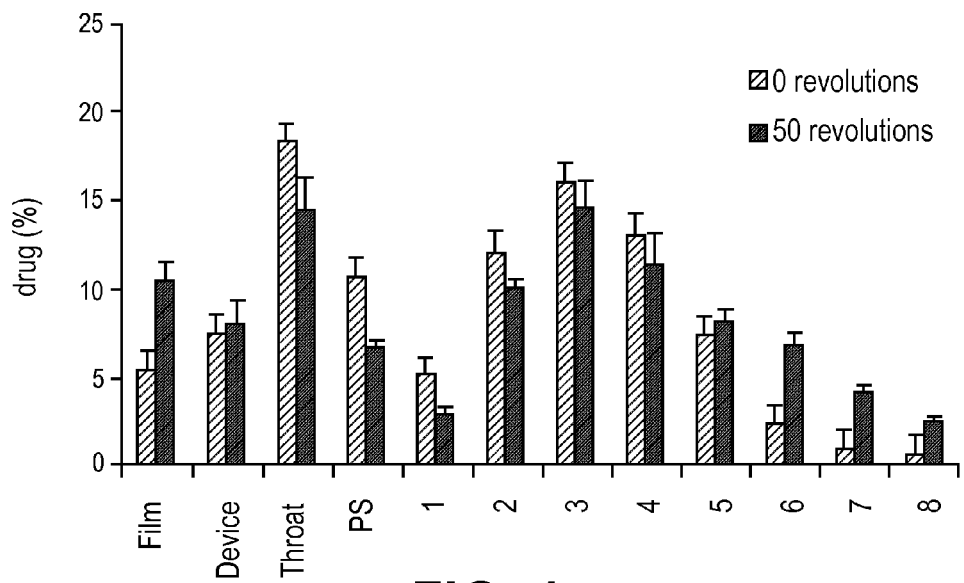
FIG. 4 is a graph illustrating the dispersion profile of drug microparticles from a film coated in accordance with exemplary apparatus and methods of the disclosure.

FIG. 4 is a graph illustrating the dispersion profile of an unrestrained flutter based slit flag flutter device at a flow rate of 60 lpm using a Next Generation Pharmaceutical Impactor (NGI) inhaler. The film used in acquiring this data was an 85 micron polyolefin and the drug used was ciprofloxacin. The drug is characterized using ultraviolet spectroscopy at a wavelength of 280 nm.

As shown in FIG. 4, the dispersion profiles are different for a stationary film (0 revolutions) and a film coated for 50 revolutions (12 rpm). Both films have been coated for the same time duration of 250 seconds. As represented in the graph, a lesser amount drug is retained on the film for the stationary film compared to that of 50 revolutions of the film. This is due to the presence of large chunks of agglomerated particles on the stationary film, which are inherently heavy and can easily come off during fluttering. As a result, these large agglomerates from the stationary film are deposited in the throat and the pre-separator (PS) region of the NGI when compared to that of the 50 revolutions film. Moreover, for the 50 revolutions film, higher drug deposition is found in stages 6-8 of the NGI, which is an indication of lower agglomeration on the film coating. This results in a relatively better aerosol performance for 50 revolutions film as compared to that of stationary film as shown in Table 3 below.

TABLE 3

| | 0 revolutions | 50 revolutions |
|---|---|---|
| FPF | 60.63 ± 3.51 | 70.65 ± 2.89 |
| RF | 52.75 ± 4.18 | 57.70 ± 4.11 |

Referring to FIG. 4, stages 1 and 2 represent the bronchii and conducting airways, while stages 3-8 represent the deep lung respiratory region. As the stage numbers increase, the aerodynamic particle sizes get smaller. For example, the pre-separator may capture drug particles greater than 10 microns, while stage 3 captures drug particles less than 5 microns, and the sizes of the particles captured in stages 4-8 may be less than those captured in stage 3. Particles sized less than 5 microns are considered to be respirable.

In FIG. 4, the fine particle fraction (FPF) represents the fraction of aerosolized particles that leave the device and are less than 5 microns (i.e., respirable and will be delivered to deep lung). Accordingly, the FPF fraction can be computed by adding the amount respirable particles of stages 3-8 and dividing that sum by the total amount of particles that leave the inhaler (i.e., sum of throat+PS+stages 1-8). The respirable fraction (RF) represents the fraction of the total amount loaded on the film that has a particle size less than 5 microns (i.e., respirable and will be delivered to deep lung). Accordingly, the RF fraction can be computed by adding the amount respirable particles of stages 3-8 and dividing that sum by the total amount of particles loaded on the film (i.e., sum of film+device+throat+PS+stages 1-8).

Figure 5:
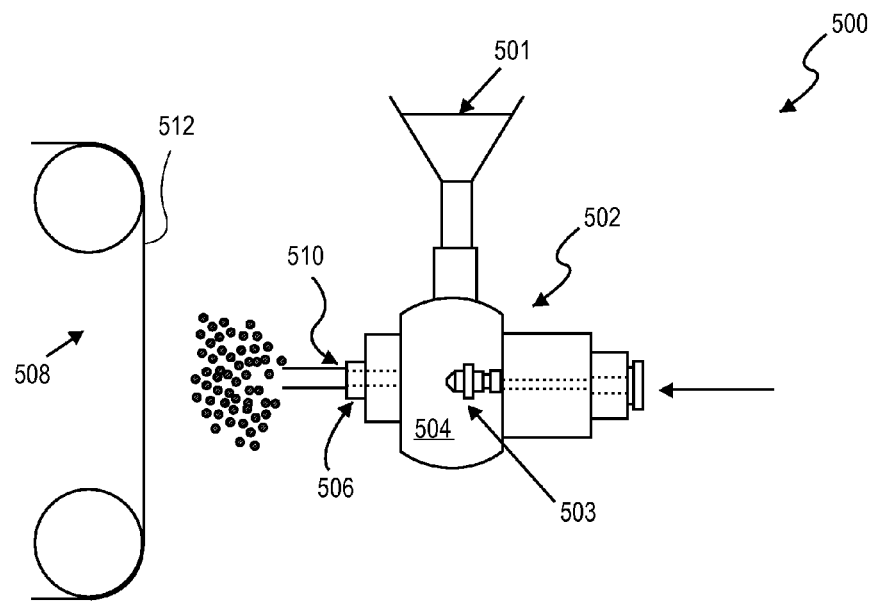
FIG. 5 is a perspective view of an exemplary deaggregation coating apparatus in accordance with various aspects of the disclosure.

Referring now to FIG. 5, an exemplary deaggregation coating apparatus 500 for microparticle dry coating of surfaces such as, for example, a film intended for use in a dry powder inhaler, is illustrated. According to various aspects, the coating apparatus 500 may include a two-fluid nozzle 502 including a feeding device 501 and a compressed air supply 503. The feeding device 501 and compressed air supply 503 may converge at a mixing region 504 where turbulent mixing of dry powder takes place. The feeding device 501 supplies dry powder having a particle size that does not need to be further milled but does need to be deaggregated. The air supply 503 assists the flow of the aggregated dry powder into the mixing region 504 where the dry powder is deaggregated to its desired micronized particle size.

The deaggregated micronized particles are directed from the mixing region 504 through an exit nozzle 506 toward a holder 508 for a surface item to be coated. The exit nozzle 506 may be similar to the exit nozzle 106 described above in reference to FIG. 1. The holder 508 may be structured and arranged to hold a surface item to be coated, such as, for example, a film, a carrier particle, or the like, proximal an exit 510 of the nozzle 506.

In operation, non-micronized and/or aggregated dry powder particles may be provided to jet mill. The jet mill is configured to micronized the dry powder particles to a desired aerodynamic diameter, for example, less than about 5 microns. The dry powder microparticles are deaggregated in the jet mill and forced out of the jet mill via pressurized airflow through an exit nozzle and onto a surface held proximal the exit of the nozzle via a holding member. In some aspects, pre-micronized dry powder particles are fed into a mixing region or cavity via a two-fluid nozzle providing pressurized air and a flow of micronized particles. The micronized particles are deaggregated in the mixing region and the deaggregated particles are forced out of the mixing region via pressurized airflow through an exit nozzle and onto a surface held proximal the exit of the nozzle via a holding member.

It should be appreciated that the direct deposition of the deaggregated microparticles onto the surface of the item to be coated prevents the reaggregation of the microparticles typical with other conventional coating systems and methods. The dry powder particles are micronized to an aerodynamic diameter having a size that can be inhaled by typical patients. Such microparticles would normally reaggreaget if collected before subsequent coating (as in a conventional jet mill). As a result, the deposition of deaggregated microparticles onto the surface of the item results in improved aerosolization during use in a dry powder inhaler because the microparticles remain deaggregated. This may improved efficiency of a dry powder inhaler that employs an item coated via the systems and methods described herein.

It should be appreciated that coating devices and methods consistent with the present disclosure may provide customized surface coating variations. It should also be appreciated that any medicament, drug, therapeutic, or other treatment particle desired to be delivered to a patient's airways is contemplated by the present disclosure. For example, the amounts (0.5 mg to several milligrams) and types of dry powders (antibiotics, long-acting beta agonists, steroids, immunosuppressives, etc.) could potentially be varied for patients and compounded based on standardized modeling of performance.

It is noted that, as used in this specification and the appended claims, the singular forms "a," "an," and "the" include plural referents unless otherwise expressly and unequivocally limited to one referent. Thus, for example, reference to "a surface" includes two or more different surfaces. As used herein, the term "include" and its grammatical variants are intended to be non-limiting, such that the recitation of items in a list is not to the exclusion of other like items that can be substituted or other items that can be added to the listed items.

It will be apparent to those skilled in the art that various modifications and variations can be made to the systems and methods of microparticle dry coating of surfaces of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A method of coating dry powder microparticles onto a surface, the method comprising:
   feeding dry powder particles comprising a medicament that is to be subsequently delivered to the lungs of a patient into a jet mill;
   milling said dry powder particles into microparticles having a desired aerodynamic diameter;
   deaggregating the microparticles in the jet mill; and
   directing said deaggregated microparticles from the jet mill through a nozzle toward a surface of a carrier to be coated, wherein the nozzle has a size and shape to control an exit velocity of the deaggregated micronized dry powder particles from the nozzle such that they contact the surface with a force that permits the powder to remain on the surface in a secure manner while still being readily removable from the surface when the surface is used in an inhaler where the dry powder particles are removed from the surface for delivery in their deaggregated state to the patient's airway.

2. The method of claim 1, further comprising holding the carrier proximal an exit of the nozzle, the carrier having said surface to be coated with deaggregated microparticles.

3. The method of claim 1, wherein the milling step comprises milling the dry powder particles into microparticles having an aerodynamic diameter of less than about 5 microns.

4. A method of temporarily coating dry powder microparticles onto a surface, the method comprising:
   feeding dry powder microparticles comprising a medicament that is to be subsequently delivered to the airways of a patient into a mixing device;
   deaggregating the microparticles in the mixing device; and
   directing said deaggregated microparticles from the mixing device through a nozzle toward a surface of a carrier to be coated, wherein the nozzle has a size and shape to control an exit velocity of the deaggregated micronized dry powder particles from the nozzle such that they contact the surface with a force that permits the powder to remain on the surface in a secure manner;
   placing the carrier into an inhaler and removing the deaggregated micronized dry powder particles from the surface to permit the dry powder particles to be delivered in their deaggregated state to the patient's airway.

5. A device for coating dry powder microparticles onto a surface, the device comprising:
   a jet mill configured to mill dry powder particles comprising a medicament to be subsequently delivered to the lungs of a patient into microparticles having a desired aerodynamic diameter and to deaggregate the microparticles;
   a feeding device structured and arranged to feed dry powder particles to the jet mill;
   a carrier comprising a surface configured to receive dry powder microparticles; and
   an exit nozzle associated with the jet mill, the exit nozzle being arranged to direct deaggregated micronized dry powder particles from the jet mill to said surface, wherein the exit nozzle has a size and shape to control an exit velocity of the deaggregated micronized dry powder particles from the exit nozzle such that they contact the surface with a force that permits the powder to remain on the surface in a secure manner while still being readily removable from the surface when the surface is used in an inhaler where the dry powder particles are removed from the surface for delivery in their deaggregated state to the patient's airway.

6. The device of claim 5, further comprising a holder structured and arranged to hold the carrier, the carrier having said surface to be coated with deaggregated microparticles.

7. The device of claim 5, wherein jet mill is configured to mill the dry powder particles into microparticles having an aerodynamic diameter of less than about 5 microns.

* * * * *

UNITED STATES PATENT AND TRADEMARK OFFICE
CERTIFICATE OF CORRECTION

PATENT NO. : 8,715,770 B2
APPLICATION NO. : 13/582883
DATED : May 6, 2014
INVENTOR(S) : Parthiban Selvam et al.

It is certified that error appears in the above-identified patent and that said Letters Patent is hereby corrected as shown below:

In the Specification:

Column 2, line 35, please delete "surfacemay" and insert -- surface may --.

Column 2, line 52, please delete "deaggreagated" and insert -- deaggregated --.

Column 2, line 58, please delete "deaggreagated" and insert -- deaggregated --.

Column 7, line 12, please delete "reaggreaget" and insert -- deaggregate --.

Column 7, line 17, please delete "improved" and insert -- improve --.

Signed and Sealed this
Twenty-third Day of September, 2014

Michelle K. Lee
*Deputy Director of the United States Patent and Trademark Office*